(12) United States Patent
Iwahama et al.

(10) Patent No.: US 7,518,021 B2
(45) Date of Patent: Apr. 14, 2009

(54) AROMATIC VINYL ETHER COMPOUNDS

(75) Inventors: Takahiro Iwahama, Himeji (JP);
Tatsuya Nakano, Himeji (JP)

(73) Assignee: Daicel Chemical Industries, Ltd., Sakai (JP)

( * ) Notice: Subject to any disclaimer, the term of this patent is extended or adjusted under 35 U.S.C. 154(b) by 0 days.

(21) Appl. No.: 10/690,527

(22) Filed: Oct. 23, 2003

(65) Prior Publication Data

US 2004/0181098 A1    Sep. 16, 2004

(30) Foreign Application Priority Data

Oct. 25, 2002  (JP)  .............. 2002-311613
Jul. 25, 2003  (JP)  .............. 2003-280504

(51) Int. Cl.
*C07C 49/786*  (2006.01)
*C07C 49/796*  (2006.01)
*C07C 43/205*  (2006.01)
*C07C 43/215*  (2006.01)
*C07C 43/23*   (2006.01)

(52) U.S. Cl. ...................... 568/333; 568/662
(58) Field of Classification Search .......... 568/662
See application file for complete search history.

(56) References Cited

U.S. PATENT DOCUMENTS 2,962,533 A * 11/1960 Hardy et al. .............. 568/333
3,215,665 A * 11/1965 Sharetts et al. ........... 524/337
3,332,924 A *  7/1967 Van De Castle et al. ... 525/355

FOREIGN PATENT DOCUMENTS

| EP | 0 167 762     | * | 1/1986 |
| EP | 0 463 862 A2  |   | 1/1992 |
| EP | 0 466 096 A1  | * | 1/1992 |
| EP | 466096        | * | 1/1992 |
| GB | 932670        | * | 7/1963 |
| JP | 62056187      | * | 3/1987 |
| JP | 05051418      | * | 3/1993 |
| JP | 7-33711 A     |   | 2/1995 |
| JP | 07-333797     | * | 12/1995 |
| WO | WO 99/10303   |   | 3/1999 |

OTHER PUBLICATIONS

Cinque et al., Structure-Activity Relationship of New Growth Inhibitors of Trypanosoma Cruzi, Journal of Medicinal Chemistry, Apr. 1998, vol. 41, No. 9, pp. 1540-1554.*

Hurd et al., Unsaturated Ethers of Pyrogallol, Sep. 1935, Journal of the American Chemical Society, vol. 57, pp. 1731-1734.*
Gent et al., Novel aromatization reaction of derivatives 1,2-0-isopropyllidene-myo-inositol, Apr. 1970, Journal of the Chemical Society [Science] C: Organic (16), pp. 2253-2255.*
machine translation of JP 05-051418, published Mar. 1993.*
Cinque et al., Structure-Activity Relationship of New Growth Inhibitors of Trypanosoma cruzi, J. Med. Chem., Apr. 1998, vol. 41, No. 9, pp. 1540-1554.*
Okimoto, et al., "Development of a Highly Efficient Catalytic Method for Synthesis of Vinyl Ethers", *J. Am. Chem. Soc.*, 124(8):1590-1591 (2002).
Ito, Patent Abstracts of Japan, Publication No. 07033711, English language abstract of JP 07/033711 A (Mar. 3, 1995).

* cited by examiner

*Primary Examiner*—Rosalynd Keys
(74) *Attorney, Agent, or Firm*—Birch, Stewart, Kolasch & Birch, LLP

(57)       ABSTRACT

Aromatic vinyl ether compounds represented by Formula (1) or by Formula (2)

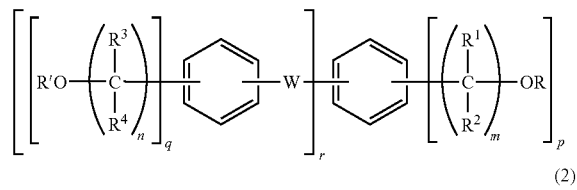

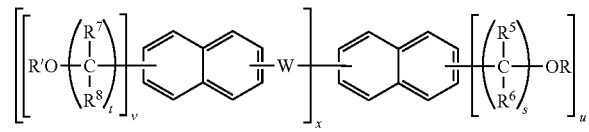

wherein each R and R' is a hydrogen atom or a group represented by Formula (3)

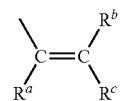

and wherein the remaining variables are as defined in the specification, provided that at least one pR in Formula (1) and at least one uR in Formula (2) is a Formula (3) group. These aromatic vinyl ether compounds are useful as, e.g., curing agents for cationic polymerization.

4 Claims, No Drawings

AROMATIC VINYL ETHER COMPOUNDS

This Nonprovisional application claims priority under 35 U.S.C. § 119(a) on Patent Application No(s). 2002-311613 and 2003-280504 filed in Japan on Oct. 25, 2002 and Jul. 25, 2003, respectively, the entire contents of which are hereby incorporated by reference.

BACKGROUND OF THE INVENTION

1. Field of the Invention

The present invention relates to aromatic vinyl ether compounds which are useful, for example, as monomers for cationic (co-) polymerization (cationic polymerization curing agents) and as raw materials for other polymers, pharmaceutical preparations, and agricultural chemicals.

2. Description of the Related Art

Epoxy resins have been conventionally used as monomers for cationic (co-)polymerization (cationic polymerization curing agents). Polymers prepared by using epoxy resins as cationic polymerization curing agents exhibit excellent adhesion and high thermal resistance. However, the epoxy resins have low cationic curing capability and exhibit very high toxicity. Accordingly, vinyl ether compounds having low toxicity and high curing capability have come to attention as cationic polymerization curing agents. Such vinyl ether compounds can be found, for example, in Japanese Unexamined Patent Application Publication No. 07-33711. However, sufficient varieties of such vinyl ether compounds have not yet been provided, and those now available are expensive. Demands have therefore been made on development of novel vinyl ether compounds.

SUMMARY OF THE INVENTION

Accordingly, an object of the present invention is to provide a novel aromatic vinyl ether compound which is useful, for example, as a cationic polymerization curing agent.

After intensive investigations to achieve the above objects, the present inventors have found that a novel aromatic vinyl ether compound can be prepared by allowing a vinyl carboxylate compound to react with a phenol or an aromatic alcohol in the presence of a specific catalyst. The present invention has been accomplished based on these findings.

Specifically, the present invention provides an aromatic vinyl ether compound represented by following Formula (1) or (2):

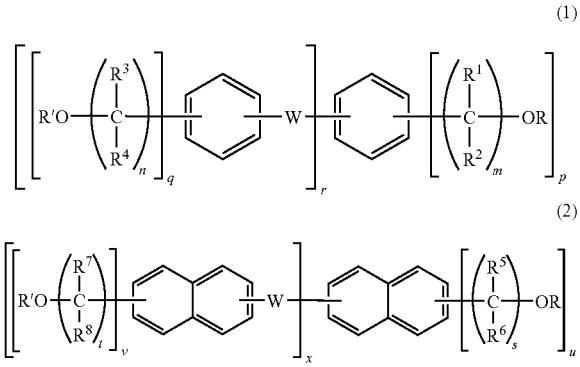

wherein R and R' may be the same or different and are each a hydrogen atom or a group represented by following Formula (3):

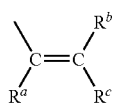

wherein $R^a$, $R^b$, and $R^c$ may be the same or different and are each a hydrogen atom or an alkyl group having 1 to 4 carbon atoms; $R^1$, $R^2$, $R^3$, $R^4$ r $R^5$, $R^6$, $R^7$, and $R^8$ may be the same or different and are each a hydrogen atom or a substituted or unsubstituted hydrocarbon group; W is a single bond or a linkage group; m is an integer of 0 to 4; n is an integer of 0 to 4; p is an integer of 1 to 6; q is an integer of 0 to 5; r is 0 or 1; s is an integer of 0 to 4; t is an integer of 0 to 4; u is an integer of 1 to 8; v is an integer of 1 to 7; and x is 0 or 1, when any of the numbers m, n, p, q, s, t, u and v is 2 or more, the resulting two or more groups may be the same or different, each substituent on the naphthalene rings shown in Formula (2) may be combined with any of eight carbon atoms constituting the naphthalene ring except the bridgehead positions, the benzene rings and naphthalene rings in the formulae may further have at least one substituent in addition to the substituents shown in the formulae, at least one of pRs in Formula (1) is the group represented by Formula (3), at least one of uRs in Formula (2) is the group represented by Formula (3), wherein, in Formula (1), p is an integer of 3 to 6 when r is 0 and m is 0; $R^1$ and $R^2$ are each a substituted or unsubstituted hydrocarbon group and $R^a$ in Formula (3) in R is an alkyl group having 1 to 4 carbon atoms when r is 0, m is 1, and p is 1; all of $R^1$, $R^2$, and $R^a$ in Formula (3) in R are not concurrently hydrogen atoms when r is 0, m is 1 and p is 2; (i) p and q are each an integer of 2 to 5 when r is 1, m is 0, n is 0, and W is a single bond or an alkylene group, (ii) p is an integer of 1 to 5 and q is an integer of 0 to 5 when r is 1, m is 0, n is 0, and W is a linkage group other than alkylene groups, wherein p is an integer of 2 to 5 when r is 1, m is 0, n is 0, W is a carbonyl group, and q is 0; and in Formula (2), u is an integer of 2 to 8 when x is 0 and s is 0.

Examples of the aromatic vinyl ether compound include (A) compounds represented by Formula (1), wherein r is 0, m is 0, and p is an integer of 3 to 6, (B) compounds represented by Formula (1), wherein r is 0; m is 1; p is 1; $R^1$ and $R^2$ may be the same or different and are each an alkyl group having 1 to 4 carbon atoms, a cycloalkyl group having 3 to 6 members or a substituted or unsubstituted phenyl group; and $R^a$ in Formula (3) in R is an alkyl group having 1 to 4 carbon atoms, (C) compounds represented by Formula (1), wherein r is 0; m is 1; p is 2, and (i) at least one of two $R^1$ s and two $R^2$ s is an alkyl group having 1 to 4 carbon atoms, a cycloalkyl group having 3 to 6 members or a substituted or unsubstituted phenyl group, or (ii) at least one of $R^a$s in Formula (3) in two Rs is an alkyl group having 1 to 4 carbon atoms, (D) compounds represented by Formula (1), wherein (i) r is 0, m is 1, and p is an integer of 3 to 6; (ii) r is 0 and m is an integer of 2 to 4; or (iii) r is 1, and $R^1$, $R^2$, $R^3$ and $R^4$ may be the same or different and are each a hydrogen atom, an alkyl group having 1 to 4 carbon atoms, a cycloalkyl group having 3 to 6 members or a substituted or unsubstituted phenyl group, and (E) compounds represented by Formula (2), wherein $R^5$, $R^6$, $R^7$, and $R^8$ may be the same or different and are each a hydrogen atom, an alkyl group having 1 to 4 carbon atoms, a cycloalkyl group having 3 to 6 members or a substituted or unsubstituted phenyl group.

The present invention further provides an aromatic vinyl ether compound represented by following Formula (1a):

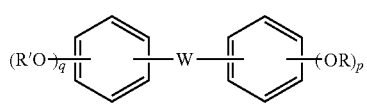

wherein R and R' may be the same or different and are each a hydrogen atom or a group represented by following Formula (3)

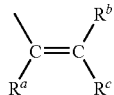

wherein $R^a$, $R^b$, and $R^c$ may be the same or different and are each a hydrogen atom or an alkyl group having 1 to 4 carbon atoms; W is a carbonyl group or a sulfonyl group; p is an integer of 1 to 5; and q is an integer of 0 to 5, wherein p is an integer of 2 to 5 when W is a carbonyl group and q is 0, wherein when any of p and q is 2 or more, the resulting two or more groups in the formula may be the same or different, wherein the benzene rings shown in the formula may each have at least one subsistent in addition to the substituents shown in the formula, and wherein at least one of pRs is the group represented by Formula (3).

The terms "vinyl ether compound(s)" and "vinyl carboxylate compound(s)" as used herein also include vinyl ether compounds and vinyl carboxylate compounds except with a substituent replacing the hydrogen atom of the vinyl group. The term "transition element(s)" as used herein means and includes Group IIIA elements, Group IVA elements, Group VA elements, Group VIA elements, Group VIIA elements, Group VIII elements, and Group IB elements of the Periodic Table of Elements.

The present invention can provide novel aromatic vinyl ether compounds which are useful, for example, as cationic polymerization curing agents.

Other and further objects, features and advantages of the present invention will be appear more fully from the following description.

DESCRIPTION OF THE PREFERRED EMBODIMENTS

Aromatic Vinyl Ether Compounds

The substituents R and R' in Formulae (1) and (2) may be the same or different and are each a hydrogen atom or a substituted or unsubstituted vinyl group represented by Formula (3). The substituents $R^a$, $R^b$ and $R^c$ in the group of Formula (3) may be the same or different and are each a hydrogen atom or an alkyl group having 1 to 4 carbon atoms. Examples of the alkyl group having 1 to 4 carbon atoms are methyl, ethyl, propyl, isopropyl, butyl, isobutyl, and t-butyl groups. $R^a$, $R^b$ and $R^c$ are each preferably hydrogen atom or methyl group.

The substituents $R^1$, $R^2$, $R^3$, $R^4$, $R^5$, $R^6$, $R^7$, and $R^8$ in Formulae (1) and (2) may be the same or different and are each a hydrogen atom or a substituted or unsubstituted hydrocarbon group. Examples of the hydrocarbon group include aliphatic hydrocarbon groups, alicyclic hydrocarbon groups, aromatic hydrocarbon groups, and groups comprising a plurality of these groups combined with each other. The aliphatic hydrocarbon groups include, but are not limited to, linear or branched-chain alkyl groups including alkyl groups each having about 1 to about 6 carbon atoms, such as methyl, ethyl, propyl, isopropyl, butyl, isobutyl, t-butyl, and hexyl groups; alkenyl groups including alkenyl groups each having about 2 to about 6 carbon atoms, such as vinyl and allyl groups; and alkynyl groups including alkynyl groups each having about 2 to about 6 carbon atoms, such as propynyl group. The alicyclic hydrocarbon groups include, but are not limited to, monocyclic or polycyclic alicyclic hydrocarbon groups each having about 3 to about 15 members, such as cyclopropyl, cyclopentyl, and cyclohexyl groups. The aromatic hydrocarbon groups include, but are not limited to, monocyclic or polycyclic aromatic hydrocarbon groups each having about 6 to about 20 carbon atoms, such as phenyl and naphthyl groups. The groups comprising a plurality of these groups combined with each other include, but are not limited to, aralkyl groups such as benzyl and 2-ethylphenyl groups.

These hydrocarbon groups may each have at least one substituent. Examples of such substituents are halogen atoms; oxo group; hydroxyl group; substituted oxy groups such as alkoxy groups, aryloxy groups, aralkyloxy groups, and acyloxy groups; carboxyl group; substituted oxycarbonyl groups such as alkoxycarbonyl groups, aryloxycarbonyl groups, and aralkyloxycarbonyl groups; substituted or unsubstituted carbamoyl groups; cyano group; nitro group; substituted or unsubstituted amino groups; sulfo group; and heterocyclic groups. The hydroxyl group, carboxyl group, and amino groups may be protected by a conventional protecting group in the field of organic synthesis.

The substituents $R^1$ with $R^2$, $R^3$ with $R^4$, $R^5$ with $R^6$, or $R^7$ with $R^8$ may be combined to form a ring with the adjacent carbon about 3 to about 8 members, such as cyclopropane ring, cyclobutane ring, cyclopentane ring, and cyclohexane ring.

Preferred examples of $R^1$, $R^2$, $R^3$, $R^4$, $R^5$, $R^6$, $R^7$, and $R^8$ are hydrogen atom; methyl, ethyl, and other alkyl groups having 1 to 4 carbon atoms; cycloalkyl groups having 3 to 6 members; and substituted or unsubstituted phenyl groups, of which hydrogen atom or methyl group is typically preferred.

In Formulae (1) and (2), W is a single bond or a linkage group. The linkage group is not specifically limited, as long as it is a divalent group, and examples are alkylene groups, alkenylene groups, arylene groups, oxygen atom (ether bond), sulfur atom (thioether bond), —NH— group which may be substituted, carbonyl group, thiocarbonyl group, sulfonyl group (—SO$_2$—), ester bond (—COO—), amide bond (—CONH—), and divalent groups comprising a plurality of these combined with each other. The alkylene groups include, but are not limited to, linear or branched-chain alkylene groups each having about 1 to about 6 carbon atoms, such as methylene, ethylene, propylene, dimethylmethylene, trimethylene, tetramethylene, pentamethylene, and hexamethylene groups. Preferred examples of W are single bond, linear or branched-chain alkylene groups each having about 1 to about 4 carbon atoms, arylene groups, oxygen atom, sulfur atom, carbonyl group, thiocarbonyl group, and sulfonyl group.

In Formulae (1) and (2), m is an integer of 0 to 4; n is an integer of 0 to 4; p is an integer of 1 to 6; q is an integer of 0 to 5; r is 0 or 1; s is an integer of 0 to 4; t is an integer of 0 to 4; u is an integer of 1 to 8; v is an integer of 1 to 7; and x is 0 or 1. When any of m, n, p, q, s, t, u and v is 2 or more, the resulting plural groups in the formulae may be the same or different. The numbers m, n, s, and t are each preferably an integer of 0 to 2 and more preferably 0 or 1. The numbers p, q, u, and v are each preferably an integer of 1 to 3. When q is 0, p is preferably an integer of 2 to 5.

The aromatic vinyl ether compounds of Formula (1a) correspond to compounds of Formula (1) wherein r is 1, m and n are 0, W is a carbonyl group or a sulfonyl group, p is an integer of 1 to 5, and q is an integer of 0 to 5, where p is an integer of 2 to 5 when W is a carbonyl group and q is 0.

The substituents on the naphthalene ring(s) shown in Formula (2) can be combined with any of eight carbon atoms constituting the naphthalene ring except the bridgehead positions. Namely, the substituents shown in Formula (2) may be combined with one of the two rings of the naphthalene ring or may be combined with the two different rings thereof.

Each of the benzene rings and naphthalene rings shown in Formulae (1), (1a) and (2) may further have at least one substituent in addition to the substituents shown in the formulae. Examples of such substituents are halogen atoms; alkyl groups including alkyl groups each having 1 to 4 carbon atoms, such as methyl, ethyl, propyl, and butyl groups; alkenyl groups including alkenyl groups each having 2 to 4 carbon atoms, such as vinyl and allyl groups; haloalkyl groups including haloalkyl groups each having 1 to 3 carbon atoms, such as chloromethyl and trifluoromethyl groups; aryl groups such as phenyl and naphthyl groups; acyl groups including acyl groups each having about 1 to about 6 carbon atoms, such as acetyl group; acyloxy groups including acyloxy groups each having about 1 to about 6 carbon atoms, such as acetoxy group; alkoxy groups including alkoxy groups each having about 1 to about 6 carbon atoms, such as methoxy and ethoxy groups; hydroxyl group; hydroxymethyl group; substituted or unsubstituted amino groups; carboxyl group; sulfo group; nitro group; and cyano group. The hydroxyl group, hydroxymethyl group, amino groups, and carboxyl group may be protected by a conventionally protecting group used in the field of organic synthesis. Among these substituents, alkyl groups, alkenyl groups, aryl groups, and other hydrocarbon groups are preferred, of which alkyl groups each having 1 to 4 carbon atoms, alkenyl groups each having 2 to 4 carbon atoms, and phenyl group are preferred. When plural substituents are substituted on the naphthalene ring, these substituents are not combined to form a ring with a carbon atom constituting the naphthalene ring. When plural substituents are substituted on the benzene ring, these substituents may be combined to form an alicyclic ring with carbon atoms constituting the benzene ring.

The aromatic vinyl ether compounds of the present invention each have at least one substituted or unsubstituted vinyl group. Specifically, at least one of pR5 in Formulae (1) and (1a) is the group of Formula (3); and at least one of uR5 in Formula (2) is the group of Formula (3). When r is 1 in Formulae (1) and (1a), all the qR's may be hydrogen atoms or at least one of qR's may be the group of Formula (3). When x is 1 in Formula (2), all the vR's may be hydrogen atoms or at least one of vR's may be the group of Formula (3).

In Formula (1), p is an integer of 3 to 6 when r is 0 and m is 0; $R^1$ and $R^2$ are each a substituted or unsubstituted hydrocarbon group and $R^a$ in Formula (3) in R is an alkyl group having 1 to 4 carbon atoms when r is 0, m is 1, and p is 1; all of $R^1$, $R^2$ and $R^a$ in Formula (3) in R are not concurrently hydrogen atoms when r is 0, m is 1 and p is 2; (i) p and q are each an integer of 2 to 5 when r is 1, m and n are 0, and W is a single bond or an alkylene group, (ii) p is an integer of 1 to 5 and q is an integer of 0 to 5 when r is 1, m and n are 0, and W is a linkage group other than alkylene groups, wherein p is an integer of 2 to 5 when r is 1, m and n are 0, W is a carbonyl group, and q is 0. Examples of the linkage group other than alkylene groups in W in (ii) are the aforementioned linkage groups other than alkylene groups, of which arylene groups, oxygen atom, sulfur atom, carbonyl group, thiocarbonyl group, and sulfonyl group are preferred. Among them, carbonyl group, thiocarbonyl group, and sulfonyl group are typically preferred. When x is 0 and s is 0 in Formula (2)., u is an integer of 2 to 8.

Preferred examples of the aromatic vinyl ether compounds are the compounds (A), (B), (C), (D) and (E), and the compounds of Formula (1a)

Typical examples of the compounds of Formula (1) are as follows:

(a) compounds wherein r is 0, m is 0, and p is an integer of 3 to 6, such as 1,3-dihydroxy-5-vinyloxybenzene, 1-hydroxy-3,5-bis(vinyloxy)benzene, 1,3,5-tris(vinyloxy)benzene, 1,3-dihydroxy-5-isopropenyloxybenzene, 1-hydroxy-3,5-bis(isopropenyloxy)benzene, 1,3,5-tris(isopropenyloxy) benzene, 1,3-dihydroxy-5-(1-propenyl)oxybenzene, 1-hydroxy-3,5-bis[(1-propenyl)oxy]benzene, and 1,3,5-tris[(1-propenyl)oxy]benzene;

(b) compounds wherein r is 0, m is 1, and p is 1, such as [1-(isopropenyloxy)-1-methylethyl]benzene, 1-[1-(isopropenyloxy)-1-methylethyl]-4-methoxybenzene, 1-carboxy-4-[1-(isopropenyloxy)-1-methylethyl]benzene, 1-acetyl-4-[1-(isopropenyloxy)-1-methylethyl]benzene, 1-[1-(isopropenyloxy)-1-methylethyl]-4-methylbenzene, 1-[1-(isopropenyloxy)-1-methylethyl]-3-methylbenzene, and 1-[1-(isopropenyloxy)-1-methylethyl]-2-methylbenzene;

(c) compounds wherein r is 0, m is 1, and p is an integer from 2 to 6, such as 1-(1-hydroxy-1-methylethyl)-3-(1-methyl-1-vinyloxyethyl)benzene, 1,3-bis(1-methyl-1-vinyloxyethyl)benzene, 1-(1-hydroxy-1-methylethyl)-3-(1-isopropenyloxy-1-methylethyl)benzene, 1,3-bis(1-isopropenyloxy-1-methylethyl)benzene, 1-(1-hydroxy-1-methylethyl)-4-(1-methyl-1-vinyloxyethyl)benzene, 1,4-bis(1-methyl-1-vinyloxyethyl)benzene, 1-(1-hydroxy-1-methylethyl)-4-(1-isopropenyloxy-1-methylethyl) benzene, 1,4-bis(1-isopropenyloxy-1-methylethyl)benzene, 1-(1-hydroxyethyl)-3-(1-vinyloxyethyl)benzene, 1,3-bis(1-vinyloxyethyl)benzene, 1-(1-hydroxyethyl)-4-(1-vinyloxyethyl)benzene, 1,4-bis(1-vinyloxyethyl)benzene, 1-(1-hydroxy-1-methylpropyl)-3-(1-methyl-1-vinyloxypropyl) benzene, 1,3-bis(1-methyl-1-vinyloxypropyl)benzene, 1-(1-hydroxy-1-methylpropyl)-4-(1-methyl-1-vinyloxypropyl) benzene, 1,4-bis(1-methyl-1-vinyloxypropyl)benzene, 1-(1-ethyl-1-hydroxypropyl)-3-(1-ethyl-1-vinyloxypropyl) benzene, 1,3-bis(1-ethyl-1-vinyloxypropyl)benzene, 1-(1-ethyl-1-hydroxypropyl)-4-(1-ethyl-1-vinyloxypropyl)benzene, 1,4-bis(1-ethyl-1-vinyloxypropyl)benzene, 1-(1-hydroxy-1-phenylethyl)-3-(1-phenyl-1-vinyloxyethyl) benzene, 1,3-bis(1-phenyl-1-vinyloxyethyl)benzene, 1-(1-hydroxy-1-phenylethyl)-4-(1-phenyl-1-vinyloxyethyl) benzene, 1,4-bis(1-phenyl-1-vinyloxyethyl)benzene, 1,3-bis(hydroxymethyl)-5-vinyloxymethylbenzene, 1-hydroxymethyl-3,5-bis(vinyloxymethyl)benzene, and 1,3,5-tris(vinyloxymethyl)benzene;

(d) compounds wherein r is 0 and m is an integer of 2 to 4, such as 2-(vinyloxy)ethylbenzene and 2-(isopropenyloxy) ethylbenzene;

(e) compounds wherein r is 1, m and n are 0, such as 3,3',5,5'-tetrakis(vinyloxy)biphenyl, bis[3,5-bis(vinyloxy) phenyl]methane, 2,2-bis[3,5-bis(vinyloxy)phenyl]propane, 3,3',5,5'-tetrakis(isopropenyloxy)biphenyl, bis[3,5-bis(isopropenyloxy)phenyl]methane, 2,2-bis[3,5-bis(isopropenyloxy)phenyl]propane, 2,4-bis(vinyloxy)phenyl phenyl ketone, 2,4-bis(isopropenyloxy)phenyl phenyl ketone, 2-hydroxy-4-vinyloxyphenyl phenyl ketone, 2-hydroxy-4-isopropenyloxyphenyl phenyl ketone, 4-hydroxy-2-vinyloxyphenyl phenyl ketone, 4-hydroxy-2-isopropenyloxyphenyl phenyl ketone, bis(2-vinyloxyphenyl) ketone, bis(2-isopropenyloxyphenyl) ketone, 2-hydroxyphenyl 2-vinyloxyphenyl ketone, 2-hydroxyphenyl 2-isopropenyloxyphenyl ketone, 4,4'-bis(vinyloxy)diphenyl sulfone, 4,4'-bis(isopropenyloxy)diphenyl sulfone, 4-hydroxy-4'-vinyloxy-diphenyl sulfone, 4-hydroxy-4'-isopropenyloxy-diphenyl sulfone, 2,4-bis(vinyloxy)phenyl 4-vinyloxyphenyl ketone [i.e., 2,4-bis(vinyloxy)phenyl(4-vinyloxyphenyl)methanone], 2-hydroxy-4-vinyloxyphenyl 4-vinyloxyphenyl ketone [i.e., 2-hydroxy-4-vinyloxyphenyl(4-vinyloxyphenyl)methanone], 4-hydroxyphenyl 2-hydroxy-4-vinyloxyphenyl ketone [i.e., 4-hydroxyphenyl(2-hydroxy-4-vinyloxyphenyl)methanone], 2,4-dihydroxyphenyl 4-vinyloxyphenyl ketone [i.e., 2,4-dihydroxyphenyl(4-vinyloxyphenyl)methanone], bis[2,4-bis(vinyloxy)phenyl] ketone [i.e., bis[2,4-bis(vinyloxy)phenyl]methanone], bis(2-hydroxy-4-vinyloxyphenyl) ketone [i.e., bis(2-hydroxy-4-vinyloxyphenyl)methanone], and 2,4-dihydroxyphenyl 2-hydroxy-4-vinyloxyphenyl ketone [i.e., 2,4-dihydroxyphenyl(2-hydroxy-4-vinyloxyphenyl)methanone;

(f) compounds wherein r is 1, and m and n are each an integer of 1 to 4, such as 4,4'-bis (1-methyl-1-vinyloxyethyl)biphenyl, bis[4-(1-methyl-1-vinyloxyethyl)phenyl]methane, 2,2-bis[4-(1-methyl-1-vinyloxyethyl)phenyl]propane, 4,4'-bis(1-isopropenyloxy-1-methylethyl)biphenyl, bis[4-(1-isopropenyloxy-1-methylethyl)phenyl]methane, 2,2-bis[4-(1-isopropenyloxy-1-methylethyl)phenyl]propane, bis[4-(1-methyl-1-vinyloxyethyl)phenyl] ether, and bis[4-(1-methyl-1-vinyloxyethyl)phenyl] ketone.

Typical examples of the compounds of Formula (2) are as follows:

(g) compounds wherein x is 0 and s is 0, such as 1-hydroxy-5-vinyloxynaphthalene, 1-hydroxy-5-isopropenyloxynaphthalene, 1,5-bis(vinyloxy)naphthalene, and 1,5-bis(isopropenyloxy)naphthalene;

(h) compounds wherein x is 0 and s is an integer of 1 to 4, such as 1-(1-methyl-1-vinyloxyethyl)naphthalene, 1-(1-isopropenyloxy-1-methylethyl)naphthalene, 1-hydroxymethyl-5-vinyloxymethylnaphthalene, 1,5-bis(vinyloxymethyl)naphthalene, 1-hydroxymethyl-5-isopropenyloxymethylnaphthalene, 1,5-bis(isopropenyloxymethyl)naphthalene, 1-(1-hydroxy-1-methylethyl)-5-(1-methyl-1-vinyloxyethyl)naphthalene, 1,5-bis(1-methyl-1-vinyloxyethyl)naphthalene, 1-(1-hydroxy-1-methylethyl)-5-(1-isopropenyloxy-1-methylethyl)naphthalene, and 1,5-bis(1-isopropenyloxy-1-methylethyl)naphthalene; and (i) compounds wherein x is 1, such as 2-hydroxy-2'-vinyloxy-1,1'-binaphthalene, 2,2'-bis(vinyloxy)-1,1'-binaphthalene, 2-hydroxy-2'-isopropenyloxy-1,1¹-binaphthalene, and 2,2'-bis(isopropenyloxy)-1,1'-binaphthalene.

Preparation of Aromatic Vinyl Ether Compounds

The aromatic vinyl ether compounds of Formula (1) including the compounds of Formula (1a) can be prepared by allowing a vinyl carboxylate compound represented by following Formula (4):

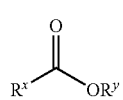

(4)

wherein $R^x$ is a hydrogen atom or a hydrocarbon group; and Ry is the group represented by Formula (3), to react with a hydroxy compound (a phenol or an aromatic alcohol) represented by following Formula (5):

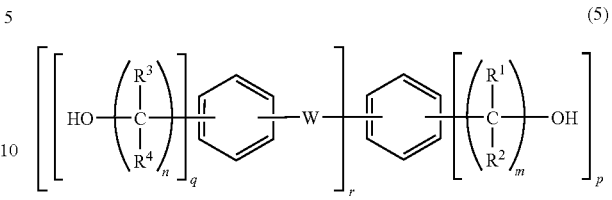

(5)

wherein each of the symbols has the same meaning as defined above, in the presence of a transition element compound (including an elementary transition element).

The aromatic vinyl ether compounds of Formula (2) can be prepared by allowing the vinyl carboxylate compound of Formula (4) to react with a hydroxy compound (a phenol or an aromatic alcohol) represented by following Formula (6):

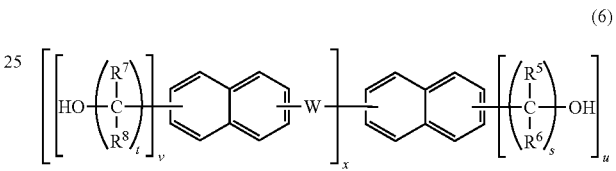

(6)

wherein each of the symbols has the same meaning as defined above, in the presence of a transition element compound (including an elementary transition element).

Each of transition element compounds can be used alone or in combination in the above processes. Examples of the transition elements are Group IIIA elements including lanthanoid elements such as lanthanum and cerium; Group IVA elements such as titanium and zirconium; Group VA elements such as vanadium; Group VIA elements such as chromium, molybdenum, and tungsten; Group VIIA elements such as manganese; Group VIII elements such as iron, cobalt, nickel, ruthenium, rhodium, palladium, osmium, iridium, and platinum; and Group IB elements such as copper and silver. Among them, Group VIII elements are preferred, of which platinum group elements such as ruthenium, rhodium, palladium, osmium, iridium, and platinum are more preferred. Above all, iridium is specifically preferred.

Examples of the transition element compound are, of transition elements, elementary substances (metals), oxides, sulfides, hydroxides, halides (fluorides, chlorides, bromides, and iodides), sulfates, oxoacids or salts thereof containing a transition element, inorganic complexes, and other inorganic compounds; cyanides, organic acid salts (e.g., acetates), organic complexes, and other organic compounds. Among them, organic complexes are preferred. Ligands for the complexes include known ligands. The valency of the transition element in the transition element compound is about 0 to about 6, and preferably about 0 to about 3. The valency of iridium in iridium compounds is preferably 1 or 3.

By taking iridium as an example, typical examples of the transition element compounds are metal iridium, iridium oxide, iridium sulfide, iridium hydroxide, iridium fluoride, iridium chloride, iridium bromide, iridium iodide, iridium sulfate, iridic acid and salts thereof (e.g., potassium iridate), inorganic iridium complexes [e.g., hexaammineiridium(III) salts, and chloropentaammineiridium(III) salts], and other inorganic compounds; iridium cyanide, organic iridium complexes [e.g., tris(acetylacetonato)iridium, dodecacarbonyltetrairidium(0), chlorotricarbonyliridium(I), di-μ-chlorotetrakis(cyclooctene)diiridium(I), di-μ-chlorotetrakis(ethylene)diiridium(I), di-μ-chlorobis(1,5-cyclooctadiene)diiridium(I), di-μ-chlorodichlorobis(pentamethylcyclopentadienyl)diiridium(III), trichlorotris(triethylphosphine)iridium(III), pentahydridobis(trimethylphosphine)iridium(V), chlorocarbonylbis(triphenylphosphine)iridium(I), chloroethylenebis(triphenylphosphine)iridium(I), (pentamethylcyclopentadienyl)dicarbonyliridium(I), bis{1,2-bis(diphenylphosphino)ethane}iridium(I) chloride, pentamethylcyclopentadienylbis(ethylene)iridium(I), carbonylmethylbis(triphenylphosphine)iridium(I), (1,5-cyclooctadiene)(diphosphine)iridium(I) halides, 1,5-cyclooctadiene(1,2-bis(diphenylphosphino)ethane)iridium(I) hexafluorophosphate, (1,5-cyclooctadiene)bis(trialkylphosphine)iridium(I) halides, bis(1,5-cyclooctadiene)iridium tetrafluoroborate, (1,5-cyclooctadiene)(acetonitrile)iridium tetrafluoroborate, and other organic compounds.

The transition element compound can be used as intact or being supported on a carrier. Examples of the carrier are conventional carriers for supporting catalysts, such as silica, alumina, silica-alumina, zeolite, titania, magnesia, and other inorganic metal oxides, as well as activated carbon. The amount of the transition element compound in a catalyst supported on a carrier is, for example, from about 0.1% by weight to about 50% by weight, and preferably from about 1% by weight to about 20% by weight relative to the carrier. The catalyst can be supported according to a conventional procedure such as impregnation, precipitation, and ion-exchange.

The amount of the transition element compound is, for example, from about 0.0001 to about 1 mole, preferably from about 0.001 to about 0.3 mole, and more preferably from about 0.005 to about 0.1 mole per 1 mole of the hydroxy compound used as a reaction component.

In Formula (4), $R^x$ is a hydrogen atom or a hydrocarbon group; and $R^y$ is the group of Formula (3). Examples of the hydrocarbon group in $R^x$ are methyl, ethyl, propyl, isopropyl, butyl, isobutyl, t-butyl, hexyl, and other alkyl groups; cyclopentyl, cyclohexyl, and other cycloalkyl groups; phenyl, and other aryl groups. Preferred examples of $R^x$ are methyl and other alkyl groups each having 1 to 4 carbon atoms and phenyl group, of which methyl group is typically preferred.

Typical examples of the vinyl carboxylate compounds of Formula (4) are vinyl acetate, isopropenyl acetate, 1-propenyl acetate, 1-methyl-1-propenyl acetate, 1,2-dimethyl-1-propenyl acetate, vinyl propionate, and isopropenyl propionate.

Hydroxy compounds corresponding to the target aromatic vinyl ether compounds of Formula (1) and (2) can be used as the hydroxy compounds of Formulae (5) and (6), respectively. The hydroxy compounds of Formulae (5) and (6) can be prepared according to a conventional procedure or can be commercially available products.

The reaction between the vinyl carboxylate compound of Formula (4) and the hydroxy compound of Formula (5) or (6) is performed in the presence of, or in the absence of, a solvent. Examples of such solvents are hexane, heptane, octane, and other aliphatic hydrocarbons; cyclohexane, and other alicyclic hydrocarbons; benzene, toluene, xylene, ethylbenzene, and other aromatic hydrocarbons; chloroform, dichloromethane, 1,2-dichloroethane, and other halogenated hydrocarbons; diethyl ether, dimethoxyethane, tetrahydrofuran, dioxane, and other ethers; acetone, methyl ethyl ketone, and other ketones; methyl acetate, ethyl acetate, isopropyl acetate, butyl acetate, and other esters; N,N-dimethylformamide, N,N-dimethylacetamide, and other amides; acetonitrile, propionitrile, benzonitrile, and other nitriles. Each of these solvents can be used alone or in combination.

The amount of the vinyl carboxylate compound of Formula (4) is, for example, from about 0.8 to about 20 equivalents, preferably from about 1 to about 15 equivalents, and more preferably from about 1.5 to about 10 equivalents per 1 equivalent of hydroxyl groups to be reacted in the hydroxy compound of Formula (5) or (6). The vinyl carboxylate compound of Formula (4) may be used in large excess.

The presence of a base in the reaction system generally significantly increases the reaction rate. The base includes inorganic bases and organic bases. Examples of the inorganic bases are alkali metal hydroxides such as lithium hydroxide, sodium hydroxide, potassium hydroxide, and cesium hydroxide; alkaline earth metal hydroxides such as magnesium hydroxide, calcium hydroxide, and barium hydroxide; alkali metal carbonates such as lithium carbonate, sodium carbonate, potassium carbonate, and cesium carbonate; alkaline earth metal carbonates such as magnesium carbonate; and alkali metal hydrogencarbonates such as lithium hydrogencarbonate, sodium hydrogencarbonate, potassium hydrogencarbonate, and cesium hydrogencarbonate.

Examples of the organic bases are organic acid salts of alkali metals including alkali metal acetates, such as lithium acetate, sodium acetate, potassium acetate, and cesium acetate; organic acid salts of alkaline earth metals, such as magnesium acetate; alkali metal alkoxides including those corresponding to the hydroxy compound of Formula (5) or (6), such as lithium methoxide, sodium methoxide, sodium ethoxide, sodium isopropoxide, and potassium ethoxide; alkali metal phenoxides such as sodium phenoxide; amines including tertiary amines, such as triethylamine and N-methylpiperidine; and nitrogen-containing aromatic heterocyclic compounds such as pyridine, 2,2'-dipyridyl, and 1,10-phenanthroline. Among these bases, those containing sodium are preferred.

The amount of the base is, for example, from about 0.001 to about 3 moles, and preferably from about 0.005 to about 2 moles per 1 mole of the hydroxy compound of Formula (5) or (6).

The reaction may be performed in the presence of a polymerization inhibitor. A reaction temperature can be set depending on, for example, the types of reaction components and the catalyst and is, for example, from about 20° C. to about 200° C., preferably from about 50° C. to about 150° C., and more preferably from about 70° C. to about 120° C. The reaction can be performed at normal atmospheric pressure, under reduced pressure or under a pressure (under a load). The atmosphere of the reaction is not specifically limited, as long as it does not adversely affect the reaction, and can be, for example, air, nitrogen gas, or argon gas atmosphere. The reaction can be performed in an any system such as batch system, semi-batch system or continuous system.

According to the above process, one or more of hydroxyl groups of the hydroxy compound of Formula (5) or (6) are vinyl-etherized to yield the corresponding aromatic vinyl ether compound of Formula (1) or (2). After the completion of the reaction, reaction products can be separated and purified by separation means such as filtration, concentration, distillation, extraction, crystallization, recrystallization, and column chromatography, as well as a combination of these separation means.

The aromatic vinyl ether compounds of the present invention can be used as monomers for cationic (co-)polymerization (cationic polymerization curing agents) and as raw materials for other polymers, pharmaceutical preparations, agricultural chemicals, and other fine chemicals. Among them, aromatic vinyl ether compounds each having plural vinyl groups can impart high solvent resistance to the resulting products and are useful as material monomers for crosslinkable resins.

The present invention will be illustrated in further detail with reference to several examples below-which are never intended to limit the scope of the invention. Reaction products were identified by GC-MS and $^1$H-NMR.

EXAMPLE 1

To a mixture of di-μ-chlorobis(1,5-cyclooctadiene)diiridium(I) [Ir(cod)Cl]$_2$ (67 mg, 0.1 mmol) and sodium carbonate (640 mg, 6 mmol) in toluene (5 ml) were added α,α,α', α'-tetramethyl-1,4-benzenedimethanol (5 mmol) and vinyl acetate (2.15 g, 25 mmol), followed by stirring at 100° C. in an atmosphere of argon gas for 6 hours. The reaction mixture was analyzed by gas chromatography to find that 1-(1-hydroxy-1-methylethyl)-4-(1-methyl-1-vinyloxyethyl)benzene and 1,4-bis(1-methyl-1-vinyloxyethyl)benzene were formed in yields of 11% and 62%, respectively, with a conversion from α,α,α',α'-tetramethyl-1,4-benzenedimethanol of 95%.

[Spectral data of 1,4-bis(1-methyl-1-vinyloxyethyl)benzene]
$^1$H-NMR (CDCl$_3$) δ: 1.65 (12H, s), 4.0-4.1 (2H, dd), 4.1-4.2 (2H, dd), 6.4-6.5 (2H, dd), 7.1 (4H, s)
MS m/e: 246, 231, 203 (40), 160 (100), 145, 91
[Spectral data of 1-(1-hydroxy-1-methylethyl)-4-(1-methyl-1-vinyloxyethyl)benzene]
MS m/e: 220, 205, 177 (100), 162, 91

EXAMPLE 2

To a mixture of di-μ-chlorobis(1,5-cyclooctadiene)diiridium(I) [Ir(cod)Cl]$_2$ (67 mg, 0.1 mmol) and sodium carbonate (640 mg, 6 mmol) in toluene (5 ml) were added α,α, α', α'-tetramethyl-1,3-benzenedimethanol (5 mmol) and vinyl acetate (2.15 g, 25 mmol), followed by stirring at 100° C. in an atmosphere of argon gas for 6 hours. The reaction mixture was analyzed by gas chromatography to find that 1-(1-hydroxy-1-methylethyl)-3-(1-methyl-1-vinyloxyethyl)benzene and 1,3-bis(1-methyl-1-vinyloxyethyl)benzene were formed in yields of 8% and 70%, respectively, with a conversion from α,α,α', α'-tetramethyl-1,3-benzenedimethanol of 98%.

[Spectral data of 1,3-bis(1-methyl-1-vinyloxyethyl)benzene]
MS m/e: 246, 231, 203 (40), 160 (100), 145, 91
[Spectral data of 1-(1-hydroxy-1-methylethyl)-3-(1-methyl-1-vinyloxyethyl)benzene]
MS m/e: 220, 205, 177 (100), 162, 91

EXAMPLE 3

To a mixture of di-μ-chlorobis(1,5-cyclooctadiene)diiridium(I) [Ir(cod)Cl]$_2$ (67 mg, 0.1 mmol) and sodium carbonate (640 mg, 6 mmol) in toluene (5 ml) were added 2-phenyl-2-propanol (5 mmol) and isopropenyl acetate (25 mmol), followed by stirring at 100° C. in an atmosphere of argon gas for 6 hours. The reaction mixture was analyzed by gas chromatography to find that (1-isopropenyloxy-1-methylethyl) benzene was formed in a yield of 78% with a conversion from 2-phenyl-2-propanol of 90%.

[Spectral data of (1-isopropenyloxy-1-methylethyl)benzene]
$^1$H-NMR (CDCl$_3$) δ: 1.6 (6H, s), 1.7 (3H, s), 3.7-3.8 (1H, d), 3.8-3.9 (1H, d), 7.1-7.3 (5H, m)
MS m/e: 176, 161, 119 (90), 91 (100), 77

EXAMPLE 4

To a mixture of di-μ-chlorobis(1,5-cyclooctadiene)diiridium(I) [Ir(cod)Cl]$_2$ (67 mg, 0.1 mmol) and sodium carbonate (640 mg, 6 mmol) in toluene (5 ml) were added 1,3,5-trihydroxybenzene (5 mmol) and vinyl acetate (2.15 g, 25 mmol), followed by stirring at 100° C. in an atmosphere of argon gas for 6 hours. The reaction mixture was analyzed by gas chromatography to find that 1,3-dihydroxy-5-vinyloxybenzene, 1-hydroxy-3,5-bis(vinyloxy)benzene, and 1,3,5-tris(vinyloxy)benzene were formed in yields of 5%, 4%, and 18%, respectively, with a conversion from 1,3,5-trihydroxybenzene of 29%.

[Spectral data of 1,3,5-tris(vinyloxy)benzene]
MS m/e: 204 (100), 175, 146, 117
[Spectral data of 1-hydroxy-3,5-bis(vinyloxy)benzene]
MS m/e: 178, 177 (100), 148
[Spectral data of 1,3-dihydroxy-5-vinyloxybenzene]
MS m/e: 152, 151, 122

EXAMPLE 5

To a mixture of di-μ-chlorobis(1,5-cyclooctadiene)diiridium(I) [Ir(cod)Cl]$_2$ (67 mg, 0.1 mmol) and sodium carbonate (640 mg, 6 mmol) in toluene (5 ml) were added 1,5-dihydroxynaphthalene (5 mmol) and vinyl acetate (2.15 g, 25 mmol), followed by stirring at 100° C. in an atmosphere of argon gas for 6 hours. The reaction mixture was analyzed by gas chromatography to find that 1-hydroxy-5-vinyloxynaphthalene and 1,5-bis(vinyloxy)naphthalene were formed in yields of 15% and 13%, respectively, with a conversion from 1,5-dihydroxynaphthalene of 30%.

[Spectral data of 1,5-bis(vinyloxy)naphthalene]
MS m/e: 212 (100), 183, 154, 151
[Spectral data of 1-hydroxy-5-vinyloxynaphthalene]
MS m/e: 186, 185 (100), 156, 153

EXAMPLE 6

To a mixture of di-μ-chlorobis(1,5-cyclooctadiene)diiridium(I) [Ir(cod)Cl]$_2$ (1.27 g, 1.9 mmol) and sodium carbonate (24.9 g, 0.23 mol)) in toluene (280 ml) were added 2,4-dihydroxybenzophenone (40 g, 0.19 mol) and vinyl propionate (75.1 g, 0.75 mol), followed by stirring at 100° C. in an atmosphere of argon gas for 3 hours. The reaction mixture was analyzed by gas chromatography to find that 2-hydroxy-4-vinyloxyphenyl phenyl ketone [i.e., 2-hydroxy-4-vinyloxyphenyl(phenyl)methanone] and 4-hydroxy-2-vinyloxyphenyl phenyl ketone [i.e., 4-hydroxy-2-vinyloxyphenyl(phenyl)methanone] were formed in yields of 90% and 2%, respectively, with a conversion from 2,4-dihydroxybenzophenone of 99%.

[Spectral data of 2-hydroxy-4-vinyloxyphenyl phenyl ketone]
$^1$H-NMR (CDCl$_3$) δ: 4.64 (1H, d), 4.9 (1H, d), 6.5 (1H, d), 6.67 (1H, S), 6.7 (1H, dd), 7.5-7.6 (6H, m), 12.5 (1H, S)
MS m/e: 240, 239, 210
[Spectral data of 4-hydroxy-2-vinyloxyphenyl phenyl ketone]
MS m/e: 240, 239, 210

EXAMPLE 7

A reaction was performed by the procedure of Example 6, except that stirring was performed for 10 hours using di-μ-chlorobis(1,5-cyclooctadiene)diiridium(I) [Ir(cod)Cl]$_2$ (3.81 g, 5.7 mmol). The reaction mixture was analyzed by gas chromatography to find that 2,4-bis(vinyloxy)phenyl phenyl ketone [i.e., 2,4-bis(vinyloxy)phenyl(phenyl)methanone] and 2-hydroxy-4-vinyloxyphenyl phenyl ketone [i.e., 2-hydroxy-4-vinyloxyphenyl(phenyl)methanone] were formed in yields of 70% and 20%, respectively, with a conversion from 2,4-dihydroxybenzophenone of 99%.

[Spectral data of 2,4-bis (vinyloxy)phenyl phenyl ketone]
$^1$H-NMR (CDCl$_3$) δ: 4.4 (2H, d), 4.7 (2H, d), 6.30 (1H, s), 6.4 (1H, dd), 6.6 (2H, dd), 7.4-7.7 (6H, m)

[Spectral data of 2-hydroxy-4-vinyloxyphenyl phenyl ketone]
$^1$H-NMR (CDCl$_3$) δ: 4.64 (1H, d), 4.9 (1H, d), 6.5 (1H, d), 6.67 (1H, S), 6.7 (1H, dd), 7.5-7.6 (6H, m), 12.5 (1H, S)
MS m/e: 240, 239, 210

EXAMPLE 8

To a mixture of di-μ-chlorobis(1,5-cyclooctadiene)diiridium(I) [Ir(cod)Cl]$_2$ (3.81 g, 5.7 mmol) and sodium carbonate (24.9 g, 0.23 mol)) in toluene (280 ml) were added 2,2'-dihydroxybenzophenone (0.19 mmol) and vinyl propionate (0.75 mol), followed by stirring at 100° C. in an atmosphere of argon gas for 10 hours. The reaction mixture was analyzed by gas chromatography to find that bis(2-vinyloxyphenyl) ketone [i.e., bis(2-vinyloxyphenyl)methanone] and 2-hydroxyphenyl 2-vinyloxyphenyl ketone [i.e., 2-hydroxyphenyl(2-vinyloxyphenyl)methanone] were formed in yields of 82% and 5%, respectively, with a conversion from 2,2'-dihydroxybenzophenone of 99%.

[Spectral data of bis(2-vinyloxyphenyl) ketone]
$^1$H-NMR (CDCl$_3$) δ: 4.4 (2H, d), 4.7 (2H, d), 6.6 (2H, dd), 6.8 (2H, d), 6.9 (2H, dd), 7.3 (2H, dd), 7.5 (2H, d)

[Spectral data of 2-hydroxyphenyl 2-vinyloxyphenyl ketone]
MS m/e: 240, 239, 210

EXAMPLE 9

To a mixture of di-μ-chlorobis(1,5-cyclooctadiene)diiridium(I) [Ir(cod)Cl]$_2$(1.27 g, 1.9 mmol) and sodium carbonate (24.9 g, 0.23 mol)) in toluene (280 ml) were added 4,4'-dihydroxydiphenyl sulfone (0.19 mol) and vinyl propionate (0.75 mol), followed by stirring at 100° C. in an atmosphere of argon gas for 3 hours. The reaction mixture was analyzed by gas chromatography to find that 4,4'-bis(vinyloxy)diphenyl sulfone and 4-hydroxy-4'-vinyloxy-diphenyl sulfone were formed in yields of 85% and 3%, respectively, with a conversion from 4,4'-dihydroxydiphenyl sulfone of 99%.

[Spectral data of 4,4'-bis(vinyloxy)diphenyl sulfone]
$^1$H-NMR (CDCl$_3$) δ: 4.4 (2H, d), 4.7 (2H, d), 6.6 (2H, dd), 6.9 (4H, d), 7.7 (4H, d)

[Spectral data of 4-hydroxy-4'-vinyloxy-diphenyl sulfone]
MS m/e: 276, 275, 246

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An aromatic vinyl ether compound represented by following Formula (1):

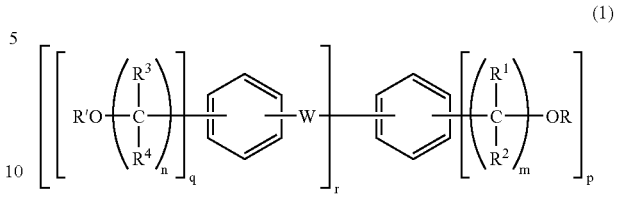

wherein:
r is 0; m is 1; and p is 2,
two Rs may be the same or different and are each a hydrogen atom or a group represented by following Formula (3):

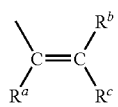

wherein R$^a$, R$^b$, and R$^c$ may be the same or different and are each a hydrogen atom or an alkyl group having 1 to 4 carbon atoms;
R$^1$, R$^2$, R$^3$, and R$^4$ may be the same or different and are each a hydrogen atom or a substituted or unsubstituted hydrocarbon group;
W is a linkage group selected from the group consisting of arylene groups, sulfur atoms, and thiocarbonyl groups;
the resulting two groups of p may be the same or different;
the benzene rings in Formula (1) may further have at least one substituent in addition to the substituents shown in the formula;
at least one of two Rs in Formula (1) is the group represented by Formula (3); and
all of R$^1$, R$^2$, and R$^a$ in Formula (3) in R are not concurrently hydrogen atoms, and wherein:
  (i) at least one of two R$^1$s and two R$^2$s is an alkyl group having 1 to 4 carbon atoms, a cycloalkyl group having 3 to 6 members or a substituted or unsubstituted phenyl group, or
  (ii) at least one of R$^a$s in Formula (3) in two Rs is an alkyl group having 1 to 4 carbon atoms.

2. The aromatic vinyl ether compound according to claim 1, which is represented by Formula (1), wherein:
r is 0; m is 1; and p is 2, and
(i) R$^1$ is a methyl group, R$^2$ is a methyl group, and
(ii) R$^a$ in Formula (3) is a hydrogen atom,
said compound being 1,4-bis(1-methyl-1-vinyloxyethyl)benzene.

3. An aromatic vinyl ether compound represented by following Formula (1a):

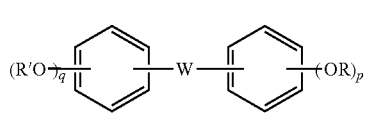

wherein
W is a carbonyl group;
R is a vinyl group;
R' is a vinyl group;
p is 2; and q is 0,
said compound being 2,4-bis(vinyloxy)phenyl phenyl ketone.

4. An aromatic vinyl ether compound represented by following Formula (1a):
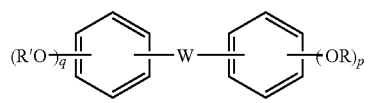
(1a)
wherein
  W is a carbonyl group;
  R is a vinyl group;
  R' is a hydrogen atom;
  p is 1; and q is 1,
said compound being 2-hydroxyphenyl 2-vinyloxyphenyl ketone.
* * * * *